US00PP25479P2

(12) United States Plant Patent
Ault

(10) Patent No.: US PP25,479 P2
(45) Date of Patent: Apr. 28, 2015

(54) ***BAPTISIA* PLANT NAMED 'SUNNY MORNING'**

(50) Latin Name: ***Baptisia* hybrid**
Varietal Denomination: Sunny Morning

(71) Applicant: James Robert Ault, Libertyville, IL (US)

(72) Inventor: James Robert Ault, Libertyville, IL (US)

(73) Assignee: Chicago Land Grows, Inc, Glencoe, IL (US)

( * ) Notice: Subject to any disclaimer, the term of this patent is extended or adjusted under 35 U.S.C. 154(b) by 167 days.

(21) Appl. No.: 13/987,051

(22) Filed: Jun. 28, 2013

(51) Int. Cl.
*A01H 5/02* (2006.01)

(52) U.S. Cl.
USPC ..... Plt./263.1

(58) Field of Classification Search
CPC ..... A01H 5/02
USPC ..... Plt./263.1, 226
See application file for complete search history.

*Primary Examiner* — June Hwu
(74) *Attorney, Agent, or Firm* — Penny J. Aguirre

(57) ABSTRACT

A new cultivar of interspecific *Baptisia* 'Sunny Morning', that is characterized by its racemes of flowers that are vibrant lemon yellow with the color retained throughout bloom, its abundance of stems that are charcoal gray in spring, its early bloom season, its dense, spreading mounded plant habit, its inflorescences that are held above the foliage, its rare fruit set, and its ability to be readily propagated from stem shoot tip cuttings.

2 Drawing Sheets

Botanical classification: *Baptisia* hybrid.
Cultivar designation: 'Sunny Morning'.

BACKGROUND OF THE INVENTION

The present invention relates to a new and distinct cultivar of hybrid *Baptisia* plant, botanically known as *Baptisia* 'Sunny Morning' and will be referred to hereafter by its cultivar name, 'Sunny Morning'. The new cultivar represents a new false indigo, an herbaceous perennial grown for landscape use.

The new invention arose from an ongoing breeding program conducted by the Inventor in Glencoe, Ill.

'Sunny Morning' originated as a seedling that arose from seed that was collected and sown from an open pollinated plant of *Baptisia sphaerocarpa* 'Screaming Yellow' (not patented) in 1998. 'Sunny Morning' was selected as a single unique plant in June of 2000. Although the male parent is unknown, it is thought to be an unnamed plant of *Baptisia alba* based on the morphological characteristics of the new cultivar and because it was the only *Baptisia* growing in proximity to the female parent.

Asexual propagation of the new cultivar was first accomplished by stem shoot tip cuttings in June of 2002 in Glencoe, Ill. under the direction of the Inventor. Asexual propagation by stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Glencoe, Ill. These attributes in combination distinguish 'Sunny Morning' as a unique cultivar of *Baptisia*.

1. 'Sunny Morning' produces racemes of flowers that are vibrant lemon yellow with the color retained throughout bloom.
2. 'Sunny Morning' exhibits an abundance of stems that are charcoal gray in spring.
3. 'Sunny Morning' blooms early in the season relative to other *Baptisia*; commencing in early to mid May in Northern Illinois.
4. 'Sunny Morning' exhibits a dense, spreading mounded plant habit.
5. 'Sunny Morning' exhibits inflorescences that are held above the foliage.
6. 'Sunny Morning' is readily propagated from stem shoot tip cuttings.
7. 'Sunny Morning' rarely sets fruit.

The female parent of 'Sunny Morning', *Baptisia sphaerocarpa* 'Screaming Yellow', differs from 'Sunny Morning' in reaching peak bloom about ten days later in the season, in having stems that are yellow-green in spring, in having flowers that are golden yellow in color, and in readily setting fruit. The probable male parent, an unnamed plant of *Baptisia alba*, differs from 'Sunny Morning' in having flowers that are white in color, in having a more upright and open plant habit, in producing less stems, and in readily setting fruit. 'Sunny Morning' can be most closely compared to the cultivars 'Solar Flare' (U.S. Plant Pat. No. 20,408) and 'Carolina Moonlight' (not patented). 'Solar Flare' is similar to 'Sunny Morning' in having yellow flowers and stems that are not yellow-green in spring. 'Solar Flare' differs from 'Sunny Morning' in having yellow flowers that develop an orange-violet cast as they mature, in having stems that have a purple cast in spring rather than charcoal, and in having less foliage at the base of the stems. 'Carolina Moonlight' is similar to 'Sunny Morning' in having stems that have charcoal coloration in spring and in having yellow flowers that are held above the foliage. 'Carolina Moonlight' differs from 'Sunny Morning' in having flowers that are more buttery yellow in color and develop a bronze to violet cast as they mature, in having a more upright and open and less dense plant habit, and in having a bloom season that is 5 to 10 days later than 'Sunny Morning'.

BRIEF DESCRIPTION OF THE DRAWINGS

The accompanying colored photographs illustrate the overall appearance and distinct characteristics of the new *Baptisia*. The photographs were taken of plants seven years in age as grown outdoors in a trial plot in Glencoe, Ill.

The photograph in FIG. 1 is a side view of 'Sunny Morning' in bloom and illustrates the plant habit and flowering habit.

Figure 1:
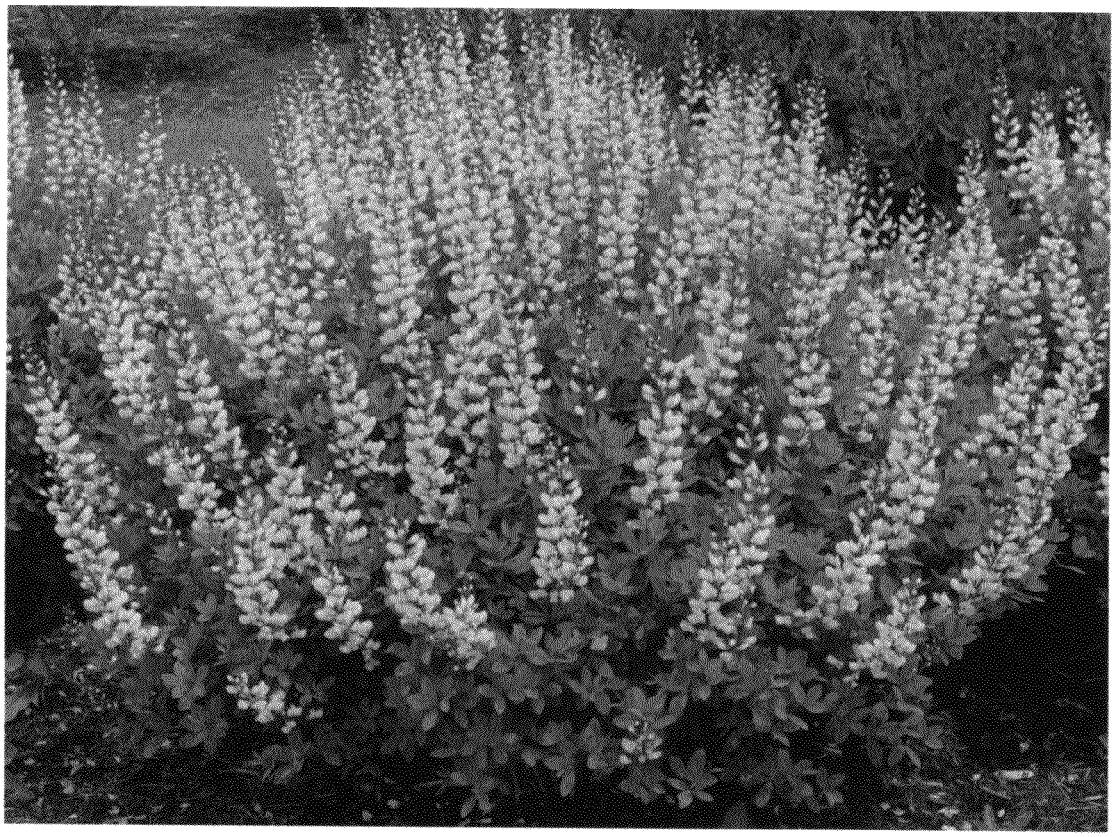
Figure 2:
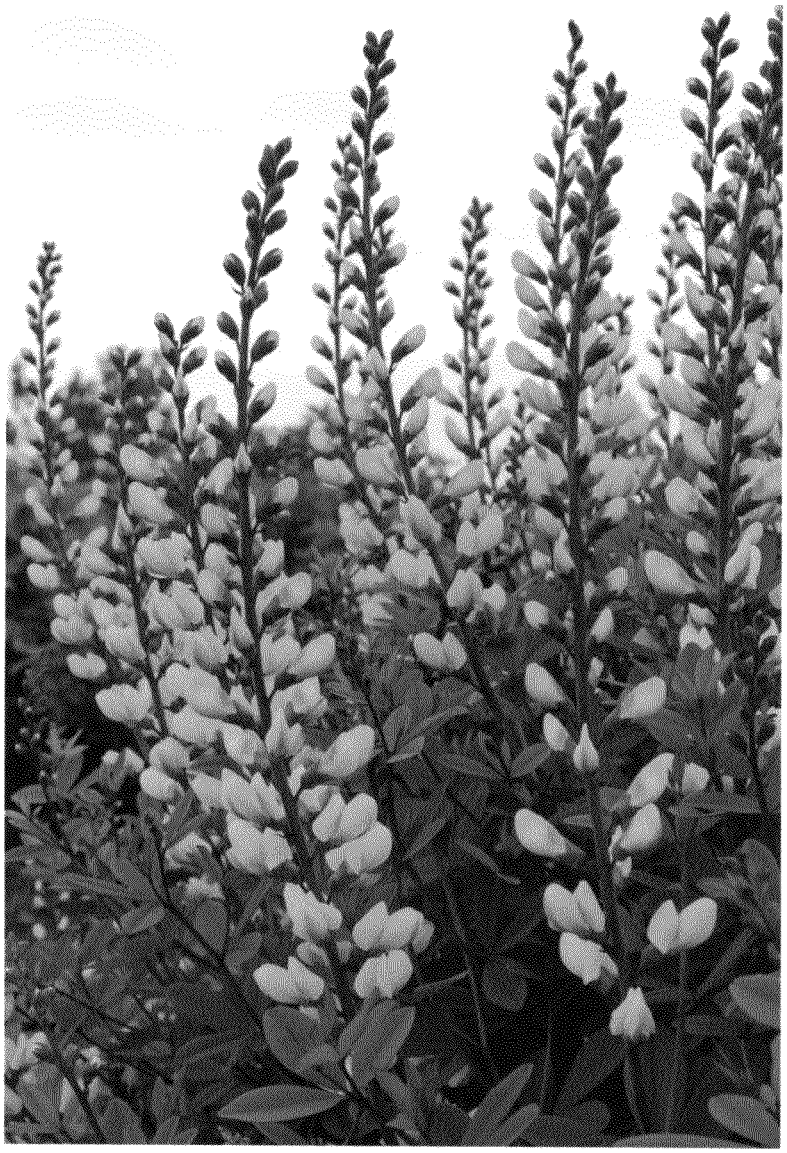

The photograph in FIG. 2 provides a close up view of the flowers of 'Sunny Morning'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of 7 to 12 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early blooming; about 3 weeks commencing in early to mid May in Glencoe, Ill.

*Plant habit.*—Dense, spreading, mounded plant habit.

*Height and spread.*—Reaches an average of 97 cm in width and 115 cm in height at 7 years in age and 97 m in height and 161 cm in width at 12 years in age.

*Hardiness.*—At least in U.S.D.A. Zones 5 to 7.

*Diseases and pests.*—No discernable disease or pest problems have been observed.

*Root description.*—Deep rooted, fibrous.

*Propagation.*—Stem shoot tip cuttings (readily propagated).

*Growth rate.*—Vigorous.

Stem description:

*Branch habit.*—Well branched; an average of 147 main stems with an average of 5 secondary branches, and an average of 2 tertiary branches per secondary branch on a 9 year-old plant, and an average of 220 main stems on a 12 year-old plant.

*Stem size.*—Main stem; average of 81 cm (including peduncle) in length and 4 mm in width (6 mm at base), secondary; average of 35 cm in length and 3 mm in width, tertiary; an average of 9 cm in length and 1.5 mm in width.

*Stem shape.*—Oval.

*Stem color.*—Young stems (spring); 138A to 138B and heavily suffused with N187A to solid N187A, mature; 138A to 138B and lightly suffused with 137A.

*Stem surface.*—Hairless, satiny, and slightly glaucous.

Foliage description:

*Leaf shape.*—Compound.

*Leaf division.*—Ternate.

*Leaf internode.*—Foliage begins 27 cm from base, an average of 6.3 cm on main stem and 5 cm on secondary branches.

*Leaf size.*—An average of 5 cm in length and 6.4 cm in width.

*Leaf quantity.*—An average of 49 per stem (including all branches).

*Leaflet shape.*—Oval.

*Leaflet base.*—Cuneate.

*Leaflet apex.*—Broadly acute to rounded and minutely retuse.

*Leaflet venation.*—Pinnate pattern not conspicuous, color on the upper and lower surface 145D with the mid rib of lower surface 145A.

*Leaflet margins.*—Entire.

*Leaf attachment.*—Petiolate.

*Leaf arrangement.*—Alternate.

*Leaflet surface.*—Glabrous on upper and lower surface.

*Leaflet color.*—Newly expanded upper and lower surface 143C in color with margins narrowly trimmed with 178A, mature; upper surface 137A and lower surface 138A in color.

*Leaflet size.*—An average of 5 cm in length and 2 cm in width.

*Petioles.*—Average of 6 mm in length and 1.2 mm in width, clasping to stem, 146C in color and lightly suffused with 178A, surface is glabrous and satiny.

*Stipules.*—Not present at all nodes, narrowly lanceolate in shape, recurved to stem, base is truncate to stem, apex is acute, average of 7 mm in length and 2 mm in width, 139C and 150B at the base in color on upper and lower surface, glabrous on upper and lower surface.

Flower description:

*Inflorescence type.*—Terminal racemes of zygomorphic flowers on main branches, blooms from the base to the apex.

*Inflorescence size.*—Average of 23 cm in length and 4.5 cm in width at mid point.

*Lastingness of inflorescence.*—About 3 weeks.

*Flower size.*—About 2.3 cm in depth and about 1.1 cm in diameter.

*Flower fragrance.*—Very faint.

*Flower number per inflorescence.*—Average of 32.

*Peduncle.*—Oval in shape, up to 21 cm in length and an average of 3.1 mm in width, 139C in color suffused with N186B to N186C, surface is glabrous, satiny and slightly glaucous, flower internode length averages about 1 mm.

*Pedicel.*—About 4 mm in length, about 0.7 mm in width, oval in shape, 138B in color suffused with N186B, glabrous and satiny surface.

*Flower buds.*—Kidney-shaped, an average of 1 cm in length and 5 mm in width, color of petal portion is 5A in color, calyx portion same as open flowers.

*Flower type.*—Papilionaceous, held at about a 70° angle to the lateral branch.

*Calyx.*—Campanulate, about 7 mm in length and 5 mm in diameter, surface is glabrous and satiny, 139C in color, lightly suffused with 178A, trimmed with 178A and 5A, persistent.

*Sepals.*—5, fused with the exception of the apex of each, free portion is triangular in shape 2 mm in width and 4 mm in depth with an acute apex, 139C in color and lightly suffused with 178A with margins of 178A and 5A (upper and lower surface), glabrous surface on upper and lower surface.

*Corolla features.*—Papilionaceous (4 segments) with a keel, a banner and 2 lateral wings, lateral wings; obovate in shape, an average of 1.5 cm in length and 7.5 mm in width, color on outer and inner surface 5A with the basal portion lightly suffused with 139C, rounded apex, oblique base, keel; only partially visible, comprised of 2 fused segments surrounding reproductive organs, obovate in shape, an average of 1.6 cm in length and 1.7 cm in width, upper and lower surface 5A in color fading to 2D at the base, apices are rounded, banner; comprised of 2 fused segments separated at the apex, reflexed, cordate apex, 1.6 cm in length and 1.6 cm in width, upper and lower surface are 5A in color with striations 166A in color along the middle of the lower surface, surface is glabrous on all sections and all petals have entire margins.

*Receptacle.*—Disk-shaped, gelatinous, 139C in color, about 2.5 mm in diameter and 2.7 mm in depth.

Reproductive organs:

*Gynoecium.*—1 Pistil, about 2 cm in length, 1.2 mm in width; style is 138C in color and 7 mm in length; stigma minute, too small to read color, ovary is superior with a stipe, 138B in color, 4 mm in length and 0.7 mm in width; stipe is 138C in color, 2 mm in length and 0.6 mm in width.

*Androcoecium.*—10 stamens, not united, 1.9 cm in length and 0.5 mm in width; filament is 1.8 cm in length, 0.5 mm in width and 139D in color; anther is dorsifixed, oval shaped, about 1 mm in length and width and 17A in color, pollen is abundant in quantity and 17A in color.

*Fruit and seed.*—Seed pods are rarely formed and no seed pods were present on the plant used for data collection.

It is claimed:

1. A new and distinct cultivar of *Baptisia* plant named 'Sunny Morning' as herein illustrated and described.

* * * * *